United States Patent [19]

Norlien et al.

[11] Patent Number: 5,038,773
[45] Date of Patent: Aug. 13, 1991

[54] FLOW METER SYSTEM

[75] Inventors: John A. Norlien, St. Paul; Michael G. Snow, Rush City, both of Minn.; A. Gerrit Crawford, San Francisco, Calif.

[73] Assignee: Medical Graphics Corporation, St. Paul, Minn.

[21] Appl. No.: 535,045

[22] Filed: Jun. 8, 1990

[51] Int. Cl.⁵ .............................................. A62B 7/00
[52] U.S. Cl. ................................ 128/205.23; 128/725
[58] Field of Search .............. 128/720, 722, 724, 725, 128/205.23; 73/861.35, 861.52

[56] References Cited

U.S. PATENT DOCUMENTS

| | | | |
|---|---|---|---|
| 2,787,999 | 4/1957 | Bennett | 128/205.23 |
| 3,098,383 | 7/1963 | West | 128/725 |
| 3,144,769 | 8/1964 | Francisco, Jr. | 73/861.35 |
| 3,196,680 | 7/1965 | Curran | 73/861.52 |
| 3,232,288 | 2/1966 | Krobath | 128/724 |
| 3,989,037 | 11/1976 | Franetzki | 128/725 |
| 4,094,508 | 6/1978 | Kirsch | 128/725 |
| 4,363,238 | 12/1982 | Willam | 128/724 |
| 4,372,169 | 2/1983 | Hughes | 73/861.52 |
| 4,403,514 | 9/1983 | Osborn | 128/725 |
| 4,765,326 | 8/1988 | Pieper | 128/205.23 |

Primary Examiner—Aaron J. Lewis
Attorney, Agent, or Firm—Haugen and Nikolai

[57] ABSTRACT

A flow meter system having a disposable mouthpiece including symmetrically disposed pitot tubes for measuring the velocity of the respiratory gases flowing through the mouthpiece and an electronic module including sensitive pressure transducers coupled to the mouthpiece and operative over a wide dynamic range provides input signals to a signal processing network for converting the pressure readings to flow information useful in cardiopulmonary performance analyzing equipment.

10 Claims, 3 Drawing Sheets

FLOW METER SYSTEM

BACKGROUND OF THE INVENTION

I. Field of the Invention

This invention relates generally to medical electronic equipment for assessing cardiopulmonary performance during exercise and for evaluating pulmonary function during static testing. More particularly, the invention relates to an improved flow measuring system which is operative over a wide dynamic range of respiratory flows as is seen in patients with differing degrees of respiratory impairment.

II. Discussion of the Prior Art

Differential pressure pneumotachographs have been in use for several decades. Typically, these devices consist of a tubular, open-ended frame with a known value flow resistive element inserted in the lumen thereof. The resistive element is generally either one or more screens positioned transverse to the direction of gas flow or a grouping of parallel capillary tubes within the gas flow. Under conditions of gas flow, this creates a pressure drop across the resistive element which can be assessed by connecting pressure taps at sequential points along the tube with a differential pressure transducer. As an example of this type of pneumotachograph is described in the Anderson et al. U.S. Pat. No. 4,463,764, the Rudolph U.S. Pat. No. 3,626,755 and published results of Fleisch (Pfluegers Arch. 209: 713-722, 1925), Lilly (Methods of Medical Research. Chicago, IL; Yearbook, 1950, 2:113-121), Pearce et al. (J. Appl. Physiol: Respirat. Environ. Exercise Physiol. 42: 968-975, 1977) and Osborn (Crit. Care, Vol. 6, No. 5: 349-351, 1978).

Although widely accepted for use, these types of pneumotachographs suffer from several problems as it relates to accurately measuring inspiratory and expiratory flow. To maintain a linear relationship between flow and the pressure drop, the resistive element must maintain laminar flow. Failure to maintain laminar flow in these types of pneumotachographs generates unpredictable linearity. These resistive elements create a back resistance to flow which can distort the measurements, particularly in patients with significant respiratory impairment. Moreover, back resistance to flow can distort the measurements. The frequency response of the pneumotachograph is important since if the change in pressure across the resistive element is out of phase with the actual flow signal, it has important significance when performing phase alignment for gas analyzers and flow signals during gas exchange measurements.

Further, after a short period of use, the screens or capillary tubes become coated with condensation and/or saliva which invariably alters the resistance value. Heating the pneumotachograph to prevent condensation helps somewhat, but complicates the calculations by cooling the resistive element unpredictably as gas flow changes. Because it is a wetted surface, the device must be replaced or decontaminated between patients. The design of the resistive elements creates a relatively high cost item which is at odds with disposability. Decontamination is both time-consuming and inconvenient as the resistive element must be thoroughly dired after cleansing.

Devices which do not employ resistive elements produce changes in pressure as a function of the square of the flow. Pressure measurement over the dynamic range dictated by patients having varying degrees of respiratory impairment.

As recommended by the various organizations such as the American Thoracic Society, American College of Chest Physicians and the National Institute for Occupational Safety and Health, measurements made from patients should be corrected to a standard environmental condition, specifically fully saturated, body temperature and pressure. Traditionally, this has been accomplished by assuming that the respiratory gases cool to ambient room temperature and applying a fixed correction of approximately 8%. It is widely known that gas cools dynamically depending upon the expiratory flow. Gas measured during high flows will more closely approximate body temperature than during low flows. This means that during high flow, the correction will be smaller than during low flow. The magnitude of this error can approach 5%. It is apparent to those skilled in the art, that a dynamic correction based upon the actual measured temperature is preferable.

Another drawback of the Hans Rudolph pneumotachograph mouthpiece is that it includes a significant dead-space leading to inaccuracies due to the patient rebreathing previously expired gas sample. This, too, distorts the readings obtained from any $O_2$ or $CO_2$ analyzer which may be coupled to the mouthpiece.

A further drawback of the prior art mouthpiece is that it tends to be a relatively high cost item. Because it embodies wetted surfaces, i.e., the screen(s) and tubular housing, it is treated as a disposable unit to avoid the possibility of the spread of harmful virus from patient-to-patient. High cost and disposability run at odds to each other.

Those skilled in the art will appreciate that when applied to respiratory gas analysis systems used in the evaluation of cardiopulmonary performance, the flow measuring system must be capable of operating over a broad dynamic range so as to be operative with patients with both healthy and sick pulmonary organs and with adults as well as infants and children.

SUMMARY OF THE INVENTION

In accordance with the present invention, a specially designed mouthpiece which can be made at low cost in a simple molding process comprises a generally tubular open-ended barrel and midway along the length of the barrel is disposed a pair of integrally molded ribs intersecting to form a cross, the ribs each including a pair of lumens which are separated from one another by a dividing wall but with the corresponding lumens of the crossing ribs being in fluid communication with one another. Each of the ribs includes a series of minute apertures at symmetrically spaced locations on opposed sides thereof. An additional pair of apertures extend through the thickness dimension of the barrel so a to intersect with the separate lumens on one of the two crossing ribs whereby tubular probes may be inserted into those lumens.

The minute apertures formed through the ribs and into their respective lumens function as pitot tubes while the probes are coupled to pressure transducers for measuring the pressure differential in the paired lumens of the ribs as respiratory gases pass over the exterior of the ribs during inspiration and expiration.

By eliminating the resistive element, the problems related to back pressure and phase lag are minimized. Further, this design permits economical manufacturing for disposability and low cost.

The flow meter mouthpiece of the present invention is adapted to be used with an electronics module which is operative over a wide dynamic range of flows, typically from, say, 20 ml/sec to 20 l/sec. While this represents a dynamic range of $10^3$ in terms of flow, it must be capable of handling a dynamic range of $10^6$ in terms of the pressure differential which is the quantity being measured in arriving at the flow value, it being understood that flow is proportional to the square root of the pressure differential.

The foregoing broad-range differential sensing can be achieved by utilizing two separate differential transducers, one for a high range of pressures, such as 0.1 to 40.0 inches $H_2O$, and a second for a low range from about 0.00005 inches to 0.5 inches $H_2O$. While the transducers themselves used in the system are commercially available, the electronics module of the present invention translates the output from these two transducers into a single signal representative of the flow through the mouthpiece. The pressure lines from the pitot tubes comprising the mouthpiece are brought in simultaneously to the low pressure transducer in a first signal processing channel and the high pressure transducer in a second signal processing channel. The output from the transducers are each applied to a first stage of amplification and to an autozero circuit which then sends a command to a second stage amplifier in each channel to effectively remove from the output of the first stage amplifier any offset existing at a time that the instrument should be reading zero.

In that the pressure reading is proportional to the square of the velocity of the respiratory gases passing over the pitot tubes and because flow is proportional to velocity to the first order, the electronic module includes an absolute value and square root circuit which is coupled to the output from the second stage amplifier and thus receives the zeroed value of the pressure reading from the low and high pressure transducers, respectively, and produces an output proportional to flow. The output from the second stage amplifiers for low pressure channel is also applied to a zero-crossing detector, which is configured to provide a logic level signal indicative of whether the input signal thereto is positive or negative relative to a threshold voltage. The output from the absolute value/square root circuit in each channel is applied to a follower/invertor which functions to buffer the output from the square root circuit while providing both a positive and a negative quantity corresponding to output from the square root stage. These two values go to a selector circuit which, in responding to the outputs of the zero-crossing detector used to restore the sign value, determines whether the positive or negative outputs from either of the follower/invertors is to be selected.

DESCRIPTION OF THE DRAWINGS

The foregoing features, objects and advantages of the invention will become apparent to those skilled in the art from the following detailed description of the preferred embodiment, especially when considered in conjunction with the accompanying drawings in which like numerals in the several views refer to corresponding parts.

DESCRIPTION OF THE PREFERRED EMBODIMENT

Figure 1:
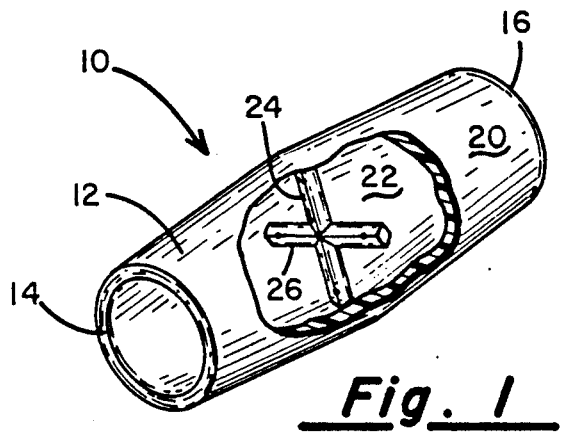
FIG. 1 is a perspective view of the mouthpiece portion of the flow meter of the present invention.
Figure 2:
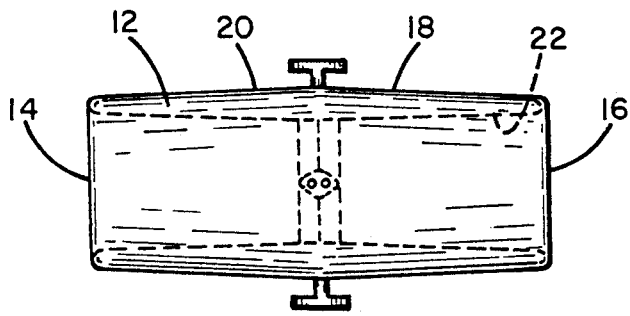
FIG. 2 is a side elevation of the mouthpiece member of FIG. 1.

Referring first to FIG. 1, there is indicated generally by numeral 10 the disposable mouthpiece portion of the flow meter system of the present invention. It is seen to comprise a generally tubular, open-ended barrel or sleeve 12 which is preferably molded or otherwise formed from suitable medical grade plastic or a metal such as stainless steel. Plastic is preferred if the mouthpiece is to be treated as a disposable and which is generally symmetric relative to a plane passing through the midsection thereof. From the view of FIG. 2, it can be seen that the wall thickness of the tubular member 12 tapers slightly from a minimum at its opposed ends 14 and 16 to a maximum proximate the midpoint 18, the slope or taper appearing on both the outer wall surface 20 and the inner wall surface 22.

Figure 5:
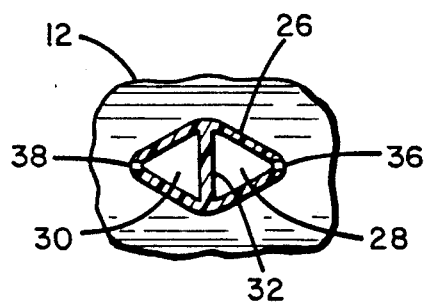
FIG. 5 is a cross-sectional view taken along the line 5—5 in FIG. 4.
Figure 3:
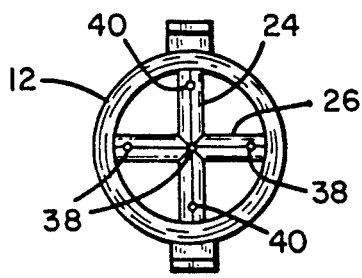
FIG. 3 is a right end view of the mouthpiece member of FIG. 1.
Figure 4:
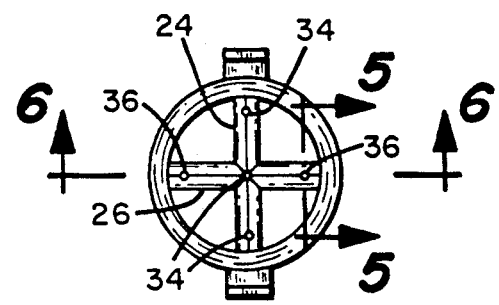
FIG. 4 is a left end view of the mouthpiece member of FIG. 1.
Figure 6:
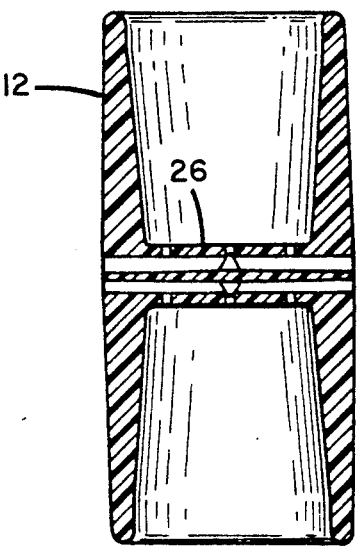
FIG. 6 is a cross-sectional view taken along the line 6—6 in FIG. 4.

Centrally disposed relative to the midpoint 18 of the tubular barrel 12 are a pair of hollow tubular ribs 24 and 26 which intersect at their midpoints to form a cross. As illustrated in the cross-sectional view of FIG. 5, each of the ribs has a pair of lumens as at 28 and 30 separated from one another by a median wall 32. While the lumens 28 and 30 of rib 26 are isolated from one another, they are individually in fluid communication with the two lumens of rib 24. Moreover, a pair of apertures 31 and 33 pass through the side wall of the tube 12 and separately into the two lumens of one of the ribs 24 or 26. The ribs have a rhombic cross-sectional configuration and formed along the opposed vertices facing the ends 14 and 16 are a series of fine apertures as at 34 and 36 in the left end view of FIG. 4 and as at 38 and 40 in the right end view of FIG. 3.

At the time of manufacture, the ports 31 and 33 formed through the side wall of the barrel or tube 12 are sealed with a dam or membrane. At the time of use, a pair of hollow needle probes (not shown) are inserted through the membrane and into the separate lumens 28 and 30 of the rib 26. The hollow needle probes are then coupled by appropriate tubing to the pressure transducers contained within the electronics module yet to be described. When the needle probes are inserted through the membrane, the material tightly surrounds the exterior of the needles creating a tight seal between the needles and the mouthpiece. Once the membranes are punctured, it provides a visual indication that the mouthpiece member has previously been used and should be discarded. It is only when the dams are intact that one can be assured that the mouthpiece has not previously bee used.

When the mouthpiece is inserted into the mouth of a patient undergoing cardiopulmonary analysis, as he or she breaths in and out, the respiratory gases pass over the cruciform rib structure and the fine apertures 34, 36, 38 and 40 function as pitot tubes, causing a pressure differential across the barrier 32 separating the pairs of intersecting lumens of the ribs 24 and 26. As is well known in the art, the pressure difference is proportional to the square of the velocity of the fluid (respiratory gases) flowing past the ribs through the central opening of the barrel or tube 12. Because of the symmetrical construction of the mouthpiece member 10, the pressure differential is found to be independent of the rotational position of the mouthpiece relative to the patient's mouth. That is to say, the pressure differential readings do not change depending upon how the ribs are positioned as the mouthpiece is inserted into the patient's mouth.

Figure 7:
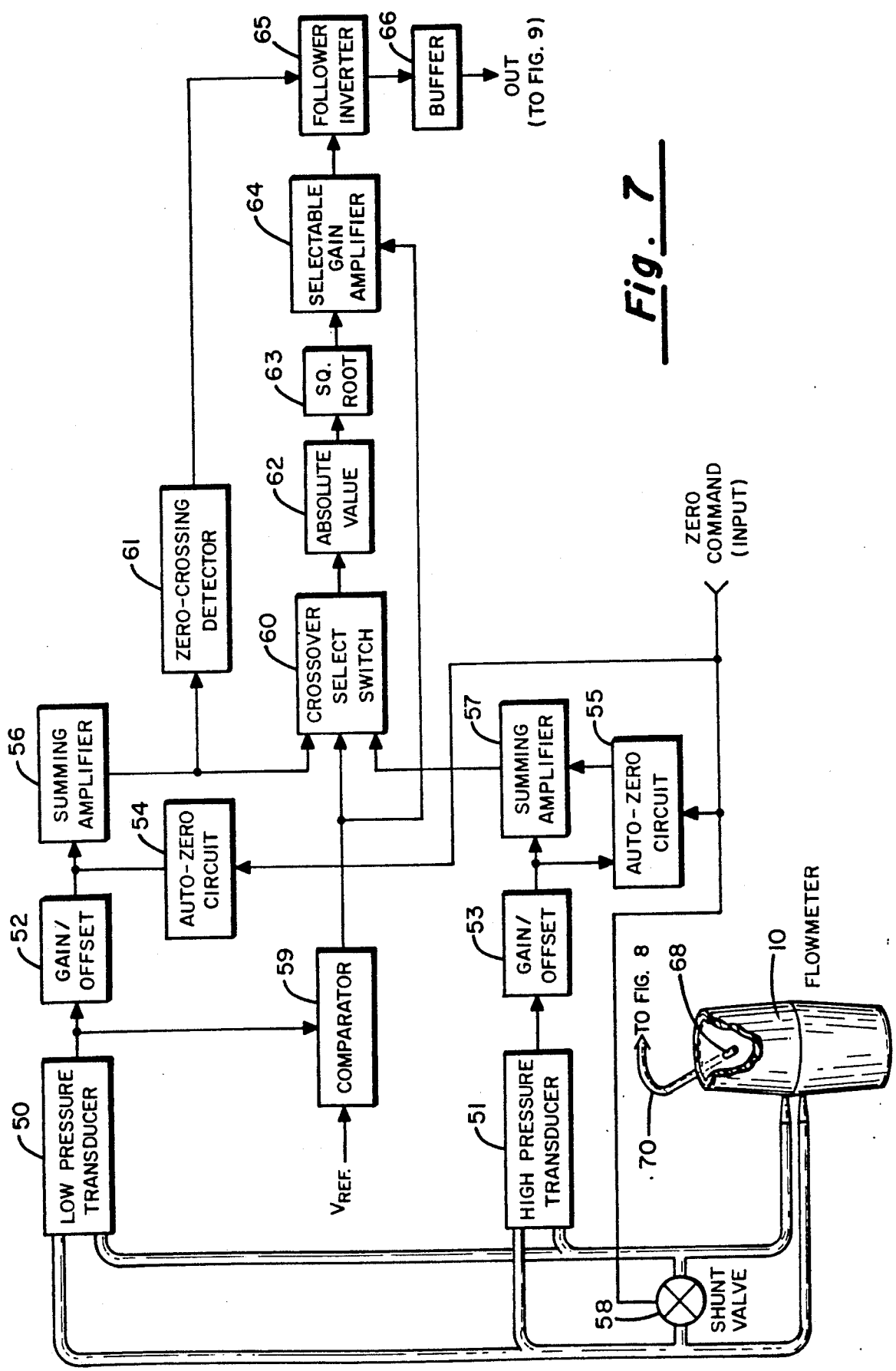
FIG. 7 is a block diagram of the electronics module which, along with the mouthpiece of FIG. 1, comprises the respiratory gas flow meter of the present invention.

Referring to FIG. 7, the mouthpiece 10 is shown as having needle probes 42 and 44 entering the sampling ports 31 and 33. The needle probes 42 and 44 are coupled by appropriate tubular lines 46 to pressure transducers in a low pressure channel and a high pressure channel.

Two transducers 50 and 51 are used to cover a pressure range of from 0.0001 to 40 inches water column. The low pressure transducer 50 has a full scale reading of about 0.5 inches water column while the high pressure transducer 51 may have a full scale of about 40 inches water column. The output of each of these transducers, after appropriate gain adjustment and offset compensation by circuits 52 and 53 comprises an analog signal with full scale output of each transducer corresponding to positive or negative 10 volts, depending upon which side of the pressure transducer is at a higher pressure than the opposite side. That is to say, during inspiration, the side of the mouthpiece ribs 24 or 26 closest to the person's mouth with be at a lower pressure than the opposed side, but during expiration, the side closest to the subject's mouth will be at a higher pressure than the downstream side.

When there is a zero pressure differential between the two sides of the mouthpiece ribs, the output of each of the transducers should be at zero volts. Should small deviations from zero occur, they can be compensated for by means of an autozero circuit 54 for the low pressure side and a corresponding circuit 55 for the high pressure side. The autozero circuits are configured so that the signal input thereto is amplified and converted to a digital value proportional to pressure which is then stored in a buffer circuit. The contents of the buffer are then converted back into an analog signal form. The analog signal is inverted and attenuated to an appropriate level so that when it is summed with the original signal in a summing amplifier, as at 56 and 57, the result will be zero volts. The contents of the buffer in the autozero circuits 54 and 55 are updated, on command, during a time interval when it is known that there is a zero pressure difference across the two needle probes. This condition is established by means of a shunt valve 58 coupled between the opposed sides of the mouthpiece ribs 24 and 26 and which is opened by the same "zero" command. As indicated above and in the drawing of FIG. 7, each of the pressure transducers 50 and 51 includes its own autozero circuit as at 54 and 55.

The output of one or the other of the transducers 50 and 51 is passed along to the next stage through a switch 60 referred to as the "crossover select switch". Switch 60 is controlled by a signal produced by a comparator 59 which is configured to monitor the output of the low pressure transducer 50. When the output of that transducer is nearly full scale in either direction, the signal from the comparator 59 changes state, so that the output of the high pressure transducer 51 will be passed through the cross-over select switch 60 instead of the low pressure signal. It should also be noted that the output of the comparator 59 is used to select a gain value at a later amplifier stage.

The amplified, zero-corrected output of the low pressure transducer at the output of summing amplifier 56 is also connected to a zero-crossing detector 61 whose output is used to re-introduce the appropriate algebraic sign in the signal at a later stage.

The signal selected by the cross-over switch 60 is applied to an analog circuit 62 that has a voltage output equal to the absolute value of the input voltage. This signal is passed to a square root circuit 63 whose voltage output is equal to the square root of the voltage applied to its input. The output of the square root circuit is amplified by a variable gain stage 64 whose value of gain is controlled by the same signal that is used to control the state of the cross-over select switch 60. The gains are adjusted so that when the pressure is just sufficient to change the signal being acted upon by the absolute value and square root circuits 62 and 63, the output of this gain stage 64 will be piecewise continuous.

Next, the signal is acted upon by a follower invertor stage 65. The output of this stage is either equal to the input to the stage, or equal to the negative of the input to this stage, depending on the output of the zero-crossing detector 61.

From the output of the follower invertor stage 65, the signal is buffered by a unity gain amplifier 66 before it is provided as the value of the flow measured in units of milliliters-per-second or liters-per-second, again depending upon whether it is the low pressure transducer 50 or high pressure transducer 51 whose output is being processed.

The flow meter 10 in FIG. 7 is shown as being partially broken away to reveal a temperature probe 68 which extends into the respiratory gas flow path through the flow meter 10. The temperature probe 68 preferably comprises a thermistor mounted through the wall of the flow meter and having electrical leads 70 leading to a circuit for producing a voltage proportional to temperature. The thermistor 68 comprises a bead of temperature sensitive resistance material which is small enough to have a short reaction time, e.g., about 150 milliseconds.

Figure 8:
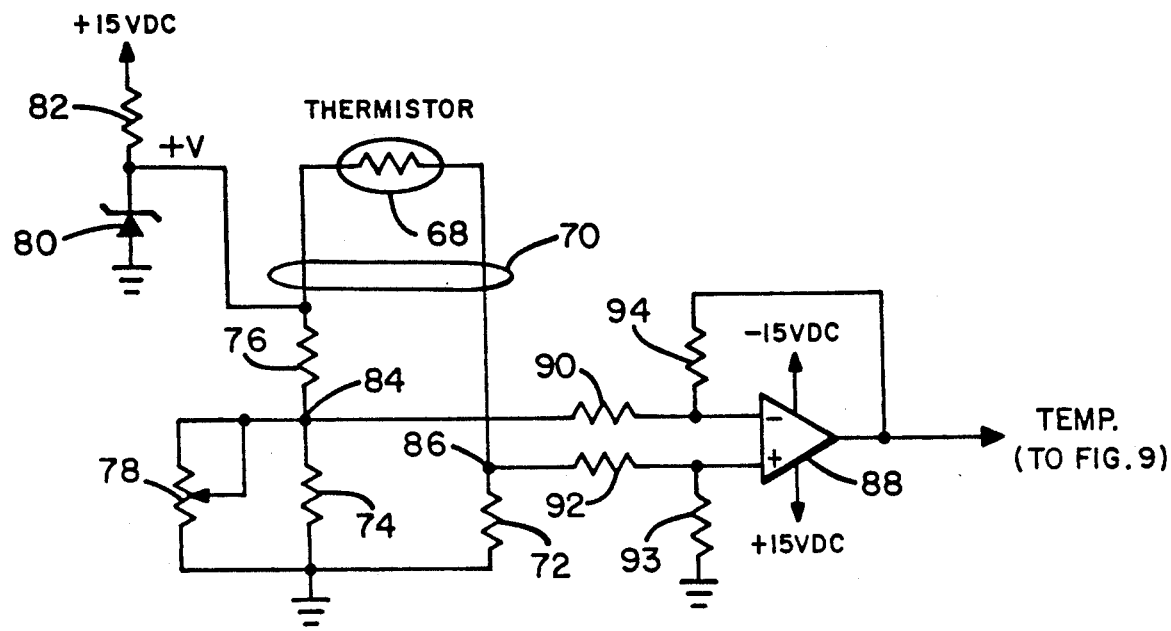
FIG. 8 is a schematic of the circuit used for monitoring the temperature of the respiratory gas flow stream and providing a signal for allowing compensation of the flow value with temperature.

Referring to FIG. 8, the thermistor 68 comprises one leg of a Wheatstone bridge which also includes fixed resistors 72, 74 and 76 and a variable resistor 78 connected in parallel with the fixed resistor 74. A fixed potential +V is derived from a regulated DC source including a zener diode 80 in series with a fixed resistor 82. The bridge output is obtained across the junction points 84–86 and is applied across the inputs of an operational amplifier 88 by way of DC coupling resistors. A feedback resistor 94 is coupled between the output from the operational amplifier 88 and the inverting input thereto. The operational amplifier 88 is configured as a variable gain amplifier with the variable resistance of the thermistor 68 controlling the overall gain of the amplifier whereby its output is directly proportional to temperature change. Specifically, an increase in temperature sensed by the thermistor element results in a decrease in its resistance which has the overall effect of increasing the output of the operational amplifier 88. Likewise, a drop in temperature sensed by the thermistor element 68 results in a increase in its resistance causing the output of the operational amplifier 88 to decrease.

From the ideal gas law, it is known that the volume of a given amount of gas varies linearly with temperature. This implies that if a volume, or flow, of gas is stated, a temperature must also be stated or implied. For a flow measuring device, such as the present invention where the temperature of the gas being measured is not a constant, it is desirable to be able to measure the temperature of the gas so that an appropriate correction to a given condition (such as "standard temperature" or "body temperature") may be calculated. Also, those skilled in the art will appreciate that for a pitot tube type of device, the pressure generated across the needle probes varies inversely with the density of the gas being measured. Gas density, in turn, varies linearly with temperature. Hence, to accurately measure a volume of gas or a flow, it is important to know the temperature of the gas in question.

Figure 9:
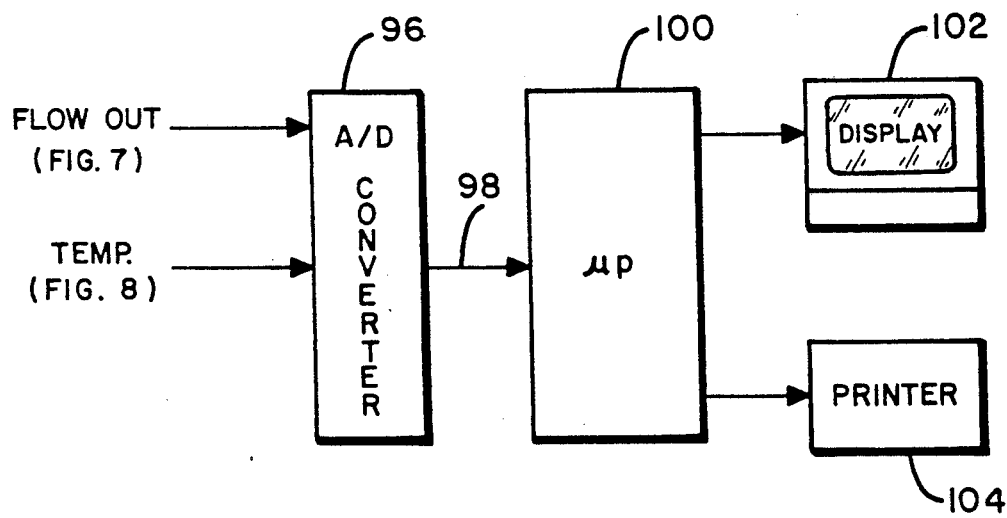
FIG. 9 is a block diagram of the digital circuit for computing and displaying respiratory flow information.

As shown in FIG. 9, the flow information output from the circuit of FIG. 7 and the temperature information from the circuit of FIG. 8 are applied to an A/D converter 96 where, on a time multiplexed basis, the flow information and temperature information are digitized and fed over a bus 98 to a microprocessor 100 which is appropriately programmed to produce an output to a display terminal 102 or to a hard copy printer 104 relating to respiratory flow in which dynamic compensation based upon temperature variations is provided for on a real-time basis.

It can be seen, then that the circuit of FIG. 7 when coupled to the mouthpiece of FIG. 1 in the fashion described, permits two separate transducers covering discrete ranges of relatively low and relatively high pressure to be used together so as to create an extremely wide dynamic range from, for example, 0.005 to 40 inches of water column and allowing the conversion of the pressure measured in this range to an analog signal proportional in amplitude to the respiratory flow through the mouthpiece, and indicating by an appropriate polarity, whether the flow is due to inspiratory or expiratory breathing.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A respiratory gas flow measuring and indicating system comprising a tubular mouthpiece member of generally circular cross-section and including two symmetrically disposed cruciform ribs extending transverse to the longitudinal dimension of said tubular mouthpiece member, said ribs each including a pair of lumens with one lumen of each pair in one rib in fluid communication with a corresponding lumen of the other pair of lumens in the other rib, each of said ribs including a plurality of symmetrically located apertures passing through the walls thereof into said pair of lumens and a further pair of apertures passing through the wall of said tubular mouthpiece member and individually aligned coaxially with said pair of lumens of one of said ribs, the passage of respiratory gases through said tubular mouthpiece member and over said cruciform ribs creating pressure differential in said pair of lumens of said one of said ribs.

2. The respiratory gas flow measuring device as in claim 1 and further including a pair of hollow needle probes insertable into said pair of apertures in said tubular mouthpiece member.

3. The respiratory gas flow measuring and indicating system as in claim 2 and further including pressure transducing means coupled in fluid communication with said hollow needle probes.

4. The respiratory gas flow measuring and indicating system as in claim 3 wherein said pressure transducing means includes a first differential pressure transducing means covering a first predetermined range of relatively high pressures and a second differential pressure transducing means covering a second predetermined range of relatively low pressures overlapping in part with said range of relatively high pressures.

5. The respiratory gas flow measuring system as in claim 4 and further including means coupled to said first and second transducing means for translating the output of said first and second transducing means into a single signal corresponding to gas flow rate through said mouthpiece member.

6. The respiratory gas flow measuring system as in claim 5 wherein said means for translating comprises a signal processing channel for each of said first and second transducing means, said signal processing channels including means for producing an analog voltage proportional to a pressure difference between said pair of lumens and means for subtracting from said analog voltage a further analog voltage obtained form said first and second transducing means when said pressure difference is zero.

7. The respiratory gas flow measuring system as in claim 6 and further including circuit means in each of said channels and coupled to the output of said subtracting means for obtaining an analog voltage proportional to the square root of said output of said subtracting means.

8. The respiratory gas flow measuring system as in claim 6 and further including polarity selecting means coupled to said circuit means in each of said channels and responsive to the direction of flow of respiratory gases through said tubular mouthpiece for affixing an algebraic sign to said analog voltage proportional to the square root of said output of said subtracting means.

9. The respiratory gas flow measuring system as in claim 1 and further including temperature sensing means operatively coupled to said mouthpiece member for measuring the temperature of respiratory gases flowing through said mouthpiece member.

10. The respiratory gas flow measuring system as in claim 7 and further including temperature sensing means operatively coupled to said mouthpiece member for producing an analog signal proportional to the temperature of the respiratory gases flowing through said mouthpiece member.

\* \* \* \* \*